United States Patent [19]

Ono

[11] Patent Number: 5,883,271

[45] Date of Patent: Mar. 16, 1999

[54] 2-SUBSTITUTED VITAMIN D DERIVATIVES

[75] Inventor: Yoshiyuki Ono, Shizuoka-ken, Japan

[73] Assignee: Chugai Seiyaku Kabushiki Kaisha, Tokyo, Japan

[21] Appl. No.: 875,292

[22] PCT Filed: Jan. 22, 1996

[86] PCT No.: PCT/JP96/00091

§ 371 Date: Oct. 8, 1997

§ 102(e) Date: Oct. 8, 1997

[87] PCT Pub. No.: WO96/22973

PCT Pub. Date: Aug. 1, 1996

[30] Foreign Application Priority Data

Jan. 23, 1995 [JP] Japan .................................. 7-042245

[51] Int. Cl.$^6$ ................................................. C07C 401/00
[52] U.S. Cl. ........................................... 552/653; 514/167
[58] Field of Search .............................. 552/563; 514/167

[56] References Cited

U.S. PATENT DOCUMENTS 4,666,634  5/1987  Miyamoto et al. .

FOREIGN PATENT DOCUMENTS

| 184206 A2 | 6/1986 | European Pat. Off. . |
| 0671411 | 9/1995 | European Pat. Off. . |
| 1267549 | 11/1986 | Japan . |
| 63107929 A2 | 5/1988 | Japan . |
| 314303 | 2/1991 | Japan . |
| 641059 | 2/1994 | Japan . |
| 9412522 A1 | 6/1994 | WIPO . |

OTHER PUBLICATIONS

Okano et al., Biological activity and conformational analysis, Proc. Workshop Vitam. D, 9th Vitamin D, 81–2, 1994.
Nobuo Ikekawa, "Structures and Biological Activities of Vitamin D Metabolites and Their Analogs", Medicinal Research Reviews, vol. 7, No. 3, pp. 333–366, 1987.

Gary H. Posner et al., "Stereocontrolled Total Synthesis of Calcitriol Derivatives: 1,25–Dihydroxy–2–(4'–Hydroxybutyl) Vitamin $D_3$ Analogs of an Osteoporosis Drug", J. Org. Chem., vol. 59, pp. 7855–7861, 1994.

Primary Examiner—Jose' G. Dees
Assistant Examiner—Alton Pryor
Attorney, Agent, or Firm—Browdy and Neimark

[57] ABSTRACT

A compound represented by general formula (I):

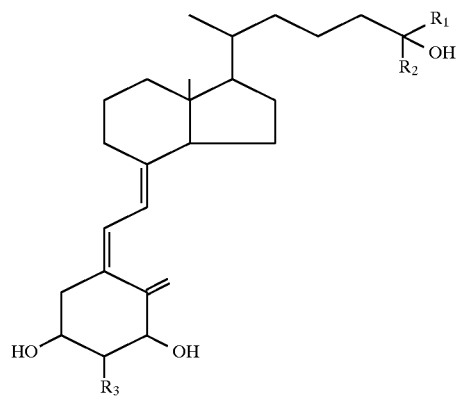

wherein $R_1$ and $R_2$, each presents an ethyl group and $R_3$ represents an alkoxy group having (1) to (7) carbon atoms which may be substituted by one or more substituents selected from a hydroxyl group, a halogen atom, a cyano group, an alkoxy group having (1) to (4) carbon atoms, an amino group and an acylamino group with the proviso that $R_1$ and $R_2$ are not a methyl group simultaneously, is disclosed.

The compound according to the present invention is useful as a pharmaceutical.

7 Claims, 1 Drawing Sheet

2-SUBSTITUTED VITAMIN D DERIVATIVES

This application is a 371 of PCT/JP6/00091 filed Jan. 22, 1996.

TECHNICAL FIELD

The present invention relates to vitamin $D_3$ derivatives having a substituent at the 2-position. More specifically, the invention relates to compounds represented by general formula (I):

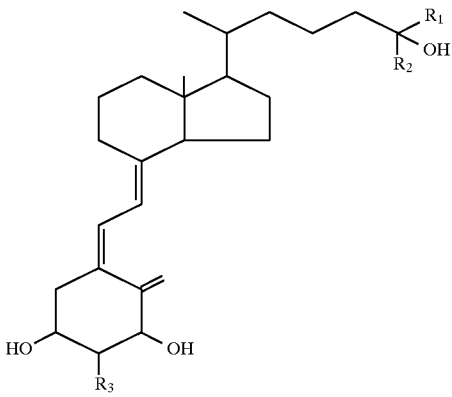

wherein $R_1$ and $R_2$, which may be the same or different, each represents an alkyl group having 1 to 4 carbon atoms and $R_3$ represents an alkoxy group having 1 to 7 carbon atoms which may be substituted by one or more substituents selected from a hydroxyl group, a halogen atom, a cyano group, an alkoxy group having 1 to 4 carbon atoms, an amino group and an acylamino group with the proviso that $R_1$ and $R_2$ are not a methyl group simultaneously.

BACKGROUND OF THE INVENTION

It has been known that an activated vitamin $D_3$ has many pharmaceutical activities such as differentiation-inducing and immunoregulating actions in addition to calcium metabolic regulatory action. Up to the present time, vitamin $D_3$ derivatives having a substituent at the 2-position have been disclosed in, for example, JP 6-23185 B and JP 6-41059 A. Among these compounds are those which are useful as a treating agent for osteoporosis.

DISCLOSURE OF THE INVENTION

In recent years, the pharmaceutical activities of vitamin D compounds have been gradually revealed. For example, 1α, 25-dihydroxy vitamin $D_3$ is known to exhibit a variety of pharmaceutical activities such as calcium metabolic regulatory action, antiproliferation and differentiation-inducing actions on cells such as tumor cells, and immunoregulatory action. Recently, numerous vitamin D derivatives have been synthesized in an attempt to separate an action from other actions exhibited by the derivatives and their pharmaceutical activities have been reviewed.

As a result of their extensive research, the present inventors have found that the compounds represented by the following general formula (I) are useful as a pharmaceutical:

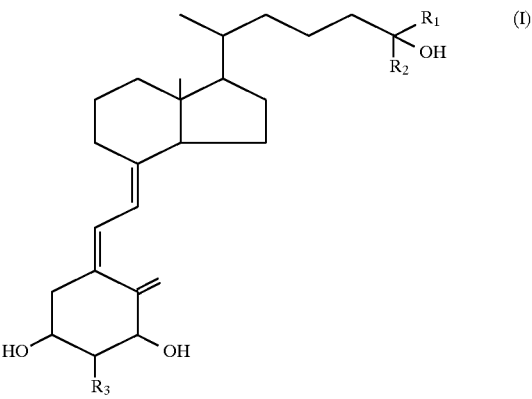

wherein $R_1$ and $R_2$, which may be the same or different, each represents an alkyl group having 1 to 4 carbon atoms and $R_3$ represents an alkoxy group having 1 to 7 carbon atoms which may be substituted by one or more substituents selected from a hydroxyl group, a halogen atom, a cyano group, an alkoxy group having 1 to 4 carbon atoms, an amino group and an acylamino group with the proviso that $R_1$ and $R_2$ are not a methyl group simultaneously.

Thus, the present invention relates to compounds represented by general formula (I):

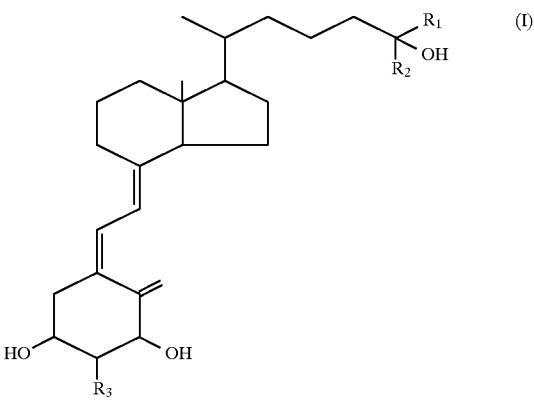

wherein $R_1$ and $R_2$, which may be the same or different, each represents an alkyl group having 1 to 4 carbon atoms and $R_3$ represents an alkoxy group having 1 to 7 carbon atoms which may be substituted by one or more substituents selected from a hydroxyl group, a halogen atom, a cyano group, an alkoxy group having 1 to 4 carbon atoms, an amino group and an acylanimo group with the proviso that $R_1$ and $R_2$ are not a methyl group simultaneously.

BEST MODE FOR CARRYING OUT THE INVENTION

Figure 1:
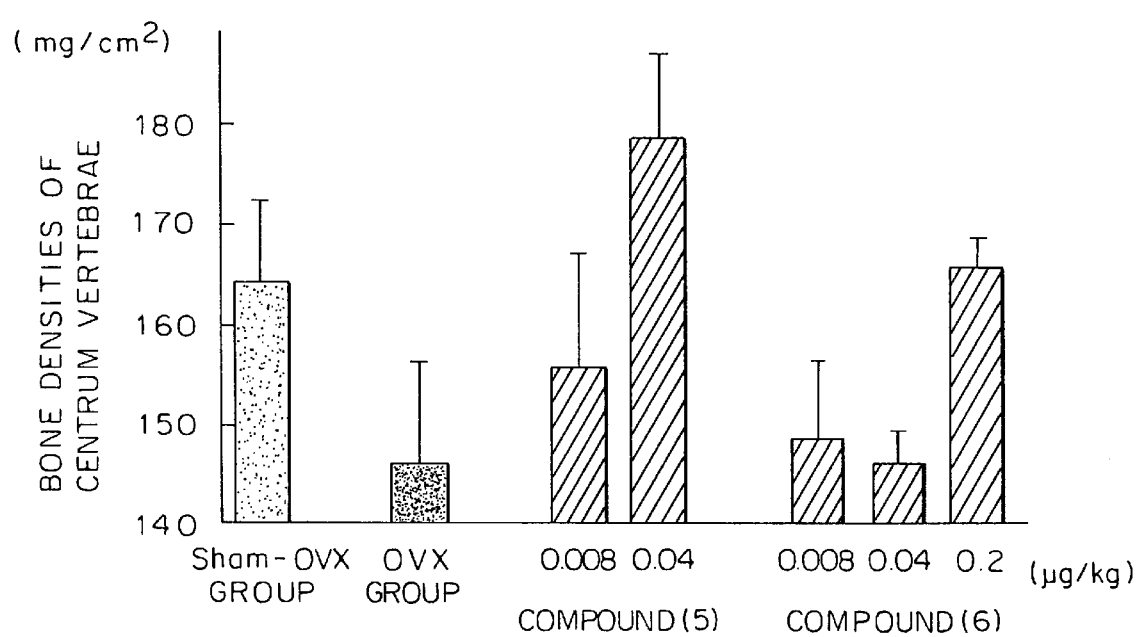
FIG. 1 is a set of graphs which illustrate the change in the amount of bone mineral density with dose of the compound according to the present invention.

Among the compounds represented by general formula (I), preferred are those in which $R_3$ is an alkoxy group having 1 to 7 carbon atoms which may be substituted by one or more hydroxyl groups.

More preferred are those in which $R_3$ is an alkoxy group having 1 to 7 carbon atoms which is substituted by one or more hydroxyl groups.

Another preferred group of the compounds represented by general formula (I) includes those represented by general formula (II):

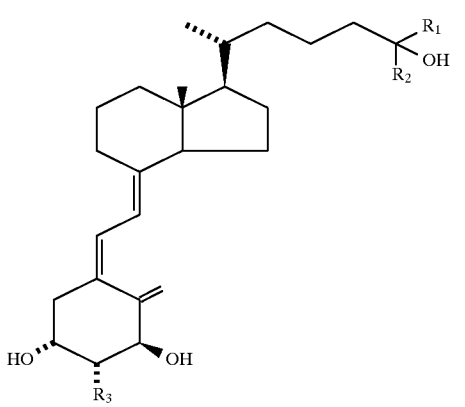

wherein $R_1$ and $R_2$, which may be the same or different, each represents an alkyl group having 1 to 4 carbon atoms and $R_3$ represents an alkoxy group having 1 to 7 carbon atoms which may be substituted by one or more substituents selected from a hydroxyl group, a halogen atom, a cyano group, an alkoxy group having 1 to 4 carbon atoms, an amino group and an acylamino group with the proviso that $R_1$ and $R_2$ are not a methyl group simultaneously.

Among these compounds, preferred are those in which $R_3$ is an alkoxy group having 1 to 7 carbon atoms which may be substituted by one or more hydroxyl groups.

More preferred are those in which $R_3$ is an alkoxy group having 1 to 7 carbon atoms which is substituted by one or more hydroxyl groups.

Furthermore preferred are those in which $R_1$ and $R_2$ are each selected from the group consisting of ethyl and n-propyl groups.

The most preferred are those represented by general formula (III):

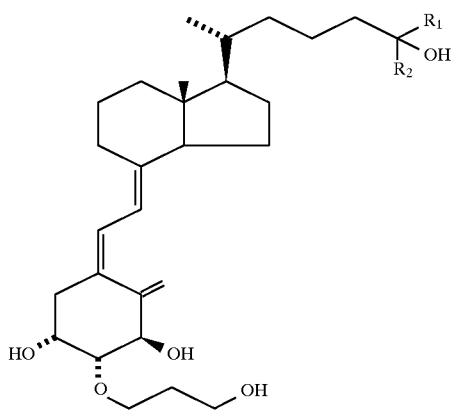

wherein $R_1$ and $R_2$, which may be the same or different, each represents ethyl or n-propyl group. Preferably $R_1$ is the same as $R_2$.

In the present invention, an alkyl group having 1 to 4 carbon atoms may be straight- or branched chain. Examples of the alkyl group include methyl, ethyl, n-propyl, i-propyl, n-butyl, i-butyl, s-butyl and t-butyl groups, preferably ethyl and n-propyl groups, more preferably ethyl group. A halogen atom is, for example, fluorine, chlorine, bromine or iodine atom, and preferably fluorine, chlorine or bromine atom, and more preferably fluorine atom. An alkoxy group having 1 to 4 carbon atoms is an alkyloxy group which may be straight- or branched chain. Examples of the alkyloxy group include methoxy, ethoxy, n-propoxy, i-propoxy, n-butoxy, i-butoxy, s-butoxy and t-butoxy groups, preferably methoxy and ethoxy groups, more preferably methoxy group.

An acylamino group represents an alkylcarbonylamino or arylcarbonylamino group which may have one or more substituents. Examples of the substituent include halogen atoms and alkoxy groups having 1 to 4 carbon atoms, preferably chlorine atom and methoxy group, respectively. Examples of the alkylcarbonylamino group which may have one or more substituents include acetylamino and trichloroacetylamino groups, and examples of the arylcarbonylamino group which may have one or more substituents include benzoylamino and p-methoxybenzoyl-amino groups. Preferred are acetylamino group, etc.

An alkoxy group having 1 to 7 carbon atoms may be a branched- or straight-chain alkyloxy group. Examples of the alkyloxy group include methoxy, ethoxy, n-propoxy, i-propoxy, n-butoxy, i-butoxy, s-butoxy, t-butoxy, pentoxy, hexyloxy and heptyloxy groups, preferably n-propoxy and n-butoxy groups, more preferably n-propoxy group.

The alkoxy group having 1 to 7 carbon atoms may be substituted by one or more substituents, but preferably by one substituent.

When the alkoxy group having 1 to 7 carbon atoms is substituted by one hydroxyl group, it may have the hydroxyl group on any carbon atom, but preferably on the terminal carbon atom.

Accordingly, preferred examples of the alkoxy group having 1 to 7 carbon atoms which is substituted by one hydroxyl group include 2-hydroxyethoxy, 3-hydroxypropoxy, 4-hydroxybutoxy, 5-hydroxypentoxy, 6-hydroxyhexyloxy and 7-hydroxyheptyloxy groups, preferably 3-hydroxypropoxy and 4-hydroxybutoxy groups, more preferably 3-hydroxypropoxy group.

The compounds according to the present invention are novel. Among the compounds, those of general formula (II) may be synthesized, for example, as shown in the following scheme:

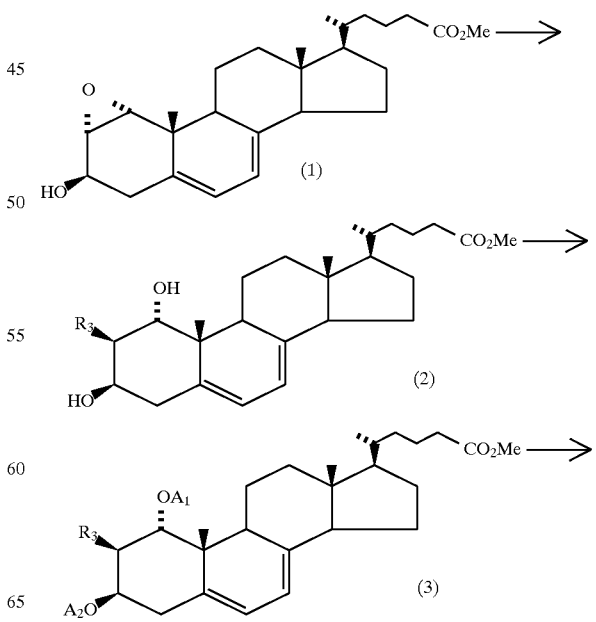

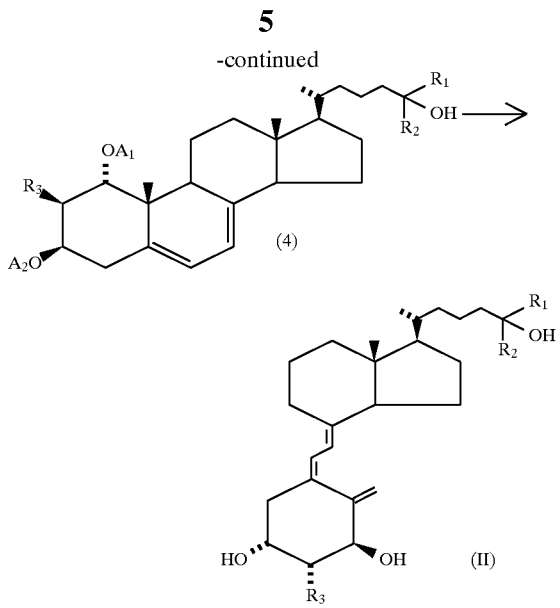

(4)

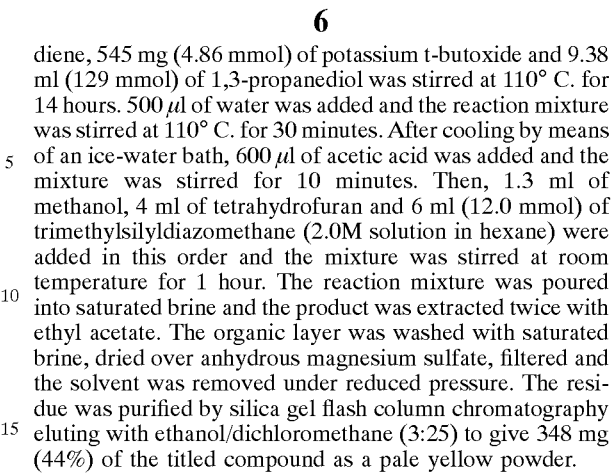

(II)

wherein $R_1$ and $R_2$, which may be the same or different, each represents an alkyl group having 1 to 4 carbon atoms and $R_3$ represents an alkoxy group having 1 to 7 carbon atoms which may be substituted by one or more substituents selected from a hydroxyl group, a halogen atom, a cyano group, an alkoxy group having 1 to 4 carbon atoms, an amino group and an acylamino group with the proviso that $R_1$ and $R_2$ are not a methyl group simultaneously; and $A_1$ and $A_2$, which may be the same or different, each represents a protecting group.

First, a substituent may be introduced into the epoxy compound (1) at the 2-position by a conventional method as described in JP 6-23185 B, JP 6-41059 A, WO94/12522, etc. Then, the hydroxyl group in the resulting compound (2) may optionally be protected with a suitable protecting group to give compound (3). Any protecting group may be used, so long as it is not reactive during the Grignard reaction described below and may be attached to or removed from the hydroxyl group without interfering with other parts of the provitamin D. However, examples of the preferred protecting group include substituted silyl groups, substituted benzyloxy groups and a methoxy-methyl group, more preferably substituted silyl groups, most preferably a t-butyldimethylsilyl group. Compound (1) which is the starting material in the above scheme may be synthesized, for example, by the method of Costa et al, J. Chem. Soc. Perkin Trans. I, pp. 1331–1336 (1985).

Next, compound (3) may be subjected to the Grignard reaction to give compound (4). Any solvent that is customarily employed in the Grignard reaction may be used in this reaction, as exemplified by an ether or aromatic hydrocarbon, preferably ether, more preferably tetrahydrofuran. Examples of the reagents which may be used in the reaction include not only usual Grignard reagents but also organolithium reagents.

After being optionally deprotected, compound (4) may be irradiated by exposure to light and then isomerized to give compound (II).

The following examples are provided in order to further illustrate the present invention but should not be construed as limiting its scope.

EXAMPLE 1

Preparation of 1α,3β-dihydroxy-2β-(3-hydroxy propoxy)-20(R)-(3-methoxycarbonylpropyl)pregna-5,7-diene A mixture of 673 mg (1.63 mmol) of 1α,2α-epoxy-3β-hydroxy-20(R)-(3-methoxycarbonylpropyl)pregna-5,7-diene, 545 mg (4.86 mmol) of potassium t-butoxide and 9.38 ml (129 mmol) of 1,3-propanediol was stirred at 110° C. for 14 hours. 500 µl of water was added and the reaction mixture was stirred at 110° C. for 30 minutes. After cooling by means of an ice-water bath, 600 µl of acetic acid was added and the mixture was stirred for 10 minutes. Then, 1.3 ml of methanol, 4 ml of tetrahydrofuran and 6 ml (12.0 mmol) of trimethylsilyldiazomethane (2.0M solution in hexane) were added in this order and the mixture was stirred at room temperature for 1 hour. The reaction mixture was poured into saturated brine and the product was extracted twice with ethyl acetate. The organic layer was washed with saturated brine, dried over anhydrous magnesium sulfate, filtered and the solvent was removed under reduced pressure. The residue was purified by silica gel flash column chromatography eluting with ethanol/dichloromethane (3:25) to give 348 mg (44%) of the titled compound as a pale yellow powder.

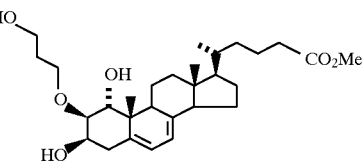

$^1$H-NMR δ: 0.62 (3H, s), 0.96 (3H, d, J=6.1 Hz), 1.06 (3H, s), 3.49–4.03(7H, m), 3.67 (3H, s), 5.30–5.41 (1H, m), 5.70 (1H, brd, J=5.4 Hz). IR (neat) cm$^{-1}$: 3385 (br), 2940, 2870, 1735, 1440, 1385, 1165, 1095, 1050, 1030. MS (m/z): 490 (M$^+$), 131 (100%). UV λmax nm: 293, 281, 271.

EXAMPLE 2

Preparation of 26,27-dimethyl-2β-(3-hydroxy propoxy)-1α,3β,25-trihydroxycholesta-5,7-diene 12 mg (24.5 µmol) of the compound prepared in Example 1 was dissolved in 2 ml of tetrahydrofuran. To the solution was added 490 µl (510µmol) of 1.04M solution of ethyl magnesium bromide in tetrahydrofuran and the mixture was stirred at room temperature for 2 hours under argon atmosphere. Water was added to the reaction mixture and the product was extracted with ethyl acetate. The organic layer was washed twice with water, dried over anhydrous magnesium sulphate, filtered and the solvent removed under reduced pressure. The residue was purified by silica gel preparative thin-layer chromatography (dichloromethane/ethanol, 10:1) to give 12 mg (95%) of the titled compound as a white powder.

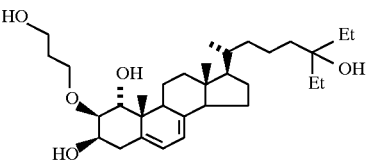

$^1$H-NMR (CDCl$_3$) δ: 0.62 (3H, s), 0.86 (6H, t, J=7.5 Hz), 0.95 (3H, d, J=6.6 Hz), 1.07 (3H, s), 3.58–4.01 (7H, m), 5.32–5.40 (1H, m), 5.67–5.73 (1H, m). UV (EtOH) nm: λmax 293, 282, 271. IR (KBr) cm$^{-1}$: 3400 (br), 2960, 2950, 2880, 1460, 1380, 1140, 1100, 1060. MS (m/z): 518 (M$^+$), 87 (100%).

EXAMPLE 3

Preparation of 26,27-dimethyl-2β-(3-hydroxy propoxy)-1α,3β,25-trihydroxy-9,10-seco-cholesta-5,7,10-(19)-triene 9.3 mg (18.0 µmol) of the compound prepared in Example 2 was dissolved in 200 ml of ethanol. While ice-cooling, the solution was irradiated with a 400 W high-pressure mercury lamp through a Vycor glass filter for 90 seconds under a stream of argon and then heated under reflux for 3.5 hours under argon atmosphere. The solvent was removed under reduced pressure and the residue was purified by silica gel preparative thin-layer chromatography (dichloromethane/ethanol, 10:1) to give 1.3 mg (14%) of the titled compound as a colorless oil.

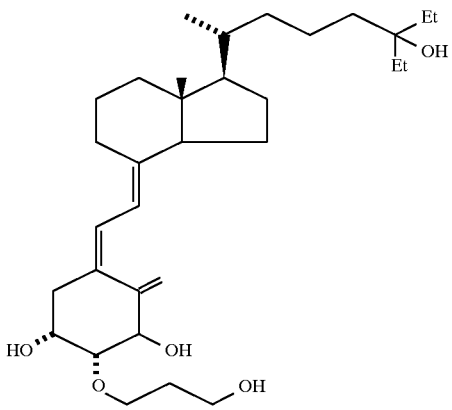

$^1$H-NMR (CDCl$_3$) δ: 0.55 (3H, s), 0.86 (6H, t, J=7.6 Hz), 0.93 (3H, d, J=6.3 Hz), 3.26 (1H, dd, J=2.8, 9.0 Hz), 3.68–3.97 (4H, m), 4.21–4.37 (2H, m), 5.08 (1H, s), 5.49 (1H, s), 6.04 (1H, d, J=11.2 Hz), 6.36 (1H, d, J=11.2 Hz). UV (EtOH) nm: λmax 264 λmin 228. IR (neat) cm$^{-1}$: 3400 (br), 2950, 2890, 1460, 1380, 1120, 1080, 760. MS (m/z): 518 (M$^+$), 87 (100%).

EXAMPLE 4

Preparation of 1α,3βi-bis(t-butyldimethyl-silyloxy)-2β-(3-t-butyldimethylsilyloxvpropoxy)-20(R)-(3-methoxycarbonylpropyl)pregna-5.7-diene To a solution of 348 mg (710 μmol) of the compound prepared in Example 1 in dichloromethane (30 ml) were added 2.19 ml (9.54 mmol) of t-butyldimethylsilyl triflate and 1.85 ml (15.9 mmol) of 2,6-lutidine and the mixture was stirred at room temperature for 1.5 hours. The reaction mixture was poured into cooled 1N hydrochloric acid and the product was extracted twice with dichloromethane. The organic layer was washed with a saturated aqueous solution of sodium hydrogen carbonate. The organic layer was dried over anhydrous magnesium sulphate, filtered and the solvent removed under reduced pressure. The residue was purified by silica gel flash column chromatography eluting with 2% ethyl acetate/n-hexane to give 541 mg (92%) of compound (16) as a colorless oil.

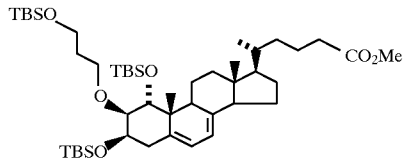

$^1$H-NMR (200MHz) δ: 0.05 (9H, s), 0.07 (3H, s), 0.10 (3H, s), 0.13 (3H, s), 0.62 (3H, s), 0.89 (27H, s), 0.96 (3H, d, J=6.3 Hz), 1.03 (3H, s), 3.49–4.12 (7H, m), 3.67 (3H, s), 5.25–5.37 (1H, m), 5.52–5.65 (1H, m). IR (neat) cm$^{-1}$: 2950, 2925, 2850, 1745, 1470, 1385, 1255, 1090, 835 MS (m/z): 832 (M$^+$), 73 (100%). UV λmax nm: 293, 281, 271.

EXAMPLE 5

Preparation of 1α,3β-bis(t-butyldimethyl-silyloxy)-26,27-diethyl-25-hydroxy-2β-(3-t-butyldimethyl-silyloxypropoxy)cholesta-5,7-diene 485 mg (1303 μmol) of cerium (III) chloride heptahydrate was dehydrated by heating to 250° C. for 2.5 hours using an electric furnace and placed in a reaction vessel to dry at 140° C. for 1 hour under reduced pressure. After purging with argon, 1 ml of tetrahydrofuran was added and the mixture was stirred at room temperature for 1 hour. 594 μl (1189 μmol) of 2M solution of propyl magnesium bromide in tetrahydrofuran was then added and the mixture was stirred at room temperature for 1 hour. Then 2 ml of a solution of the compound prepared in Example 4 in tetrahydrofuran was added and the mixture was heated under reflux for 14 hours. Water was added to the reaction mixture and the product was extracted with ethyl acetate. The organic layer was washed twice with water, dried over anhydrous magnesium sulphate, filtered and evaporated under reduced pressure. The residue was purified by silica gel preparative thin-layer chromatography (ethyl acetate/hexane, 1:5) to give 49 mg (94%) of the titled compound as a colorless oil.

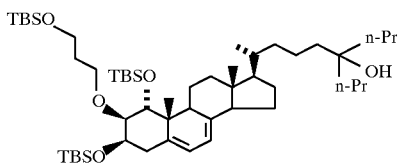

$^1$H-NMR (CDCl$_3$) δ: 0.05–0.12 (18H, m), 0.62 (3H, s), 0.81–0.92 (36H, m), 1.03 (3H, s), 3.50–4.10 (7H, m), 5.28–5.34 (1H, m), 5.54–5.50 (1H, m). UV (EtOH) nm: λmax 293, 282, 271. IR (neat) cm$^{-1}$: 3450 (br), 2950, 2930, 2850, 1460, 1080, 830, 770.

EXAMPLE 6

Preparation of 26,27-diethyl-2β-(3-hydroxy propoxy)-1α,3β,25-trihydroxycholesta-5,7-diene 49 mg (54.4 μmol) of the compound prepared in Example 5 was dissolved in 2 ml of tetrahydrofuran. To the solution was added 814 μl (814 μmol) of 1M solution of tetrabutyl ammonium fluoride in tetrahydrofuran and the mixture was heated under reflux for 2 hours under argon atmosphere. Ethyl acetate was added to the reaction mixture. The organic layer was washed twice with water, dried over anhydrous magnesium sulphate, filtered and evaporated under reduced pressure. The residue was purified by silica gel preparative thin-layer chromatography (dichloromethane/ethanol, 10:1) to give 12 mg (40%) of the titled compound as a white powder.

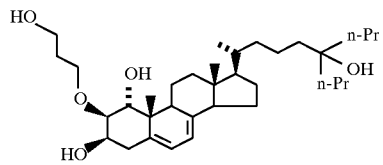

$^1$H-NMR (CDCl$_3$) δ: 0.63 (3H, s), 0.91–0.99 (9H, m), 1.07 (3H, s), 3.67–4.00 (7H, m), 5.34–5.40 (1H, m), 5.67–5.72 (1H, m). UV (EtOH) nm: λmax 293, 281, 271. IR (neat) cm$^{-1}$: 3400 (br), 2950, 2870, 1470, 1380, 1100, 1060, 760. MS (m/z): 546 (M$^+$), 56 (100%).

EXAMPLE 7

Preparation of 26,27-diethyl-2β-(3-hydroxy propoxy)-1α,3β,25-trihydroxy-9,10-seco-cholesta-5,7,10-(19)-triene 12 mg (22.1 μmol) of the compound prepared in Example 6 was dissolved in 200 ml of ethanol. While ice-cooling, the solution was irradiated with a 400 W high-pressure mercury lamp through a Vycor glass filter for 90 seconds under a stream of argon and then heated under reflux for 3.5 hours under argon atmosphere. The solvent was removed under reduced pressure and the residue was purified by silica gel preparative thin-layer chromatography (dichloromethane/ethanol, 10:1) to give 2.2 mg (18%) of the titled compound as a white powder.

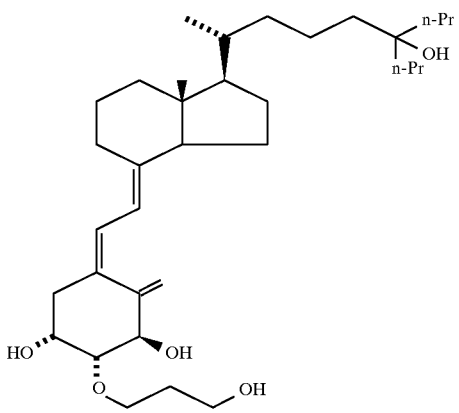

$^1$H-NMR (CDCl$_3$) δ: 0.55 (3H, s), 0.87–0.94 (9H, m), 3.27 (1H, dd, J=3.0, 8.9 Hz), 3.70–3.97 (4H, m), 4.23–4.35 (2H, m), 5.08 (1H, s), 5.49 (1H, s), 6.04 (1H, d, J=11.2 Hz), 6.36 (1H, d, J=11.2 Hz). UV (EtOH) nm: λmax 264 λmin 228. IR (neat) cm$^{-1}$: 3400 (br), 2960, 2940, 2880, 1110, 1080. MS (m/z): 546 (M$^+$), 56 (100%).

TEST EXAMPLE

Bone mineral density increasing effect in osteoporosis model rat

Eight-week old Wistar-Imamichi rats were subjected to ovariectomy (OVX) or sham-OVX. After a recuperation period of 2 weeks, the OVX rats were orally received the compound prepared in Example 3, compound (5):

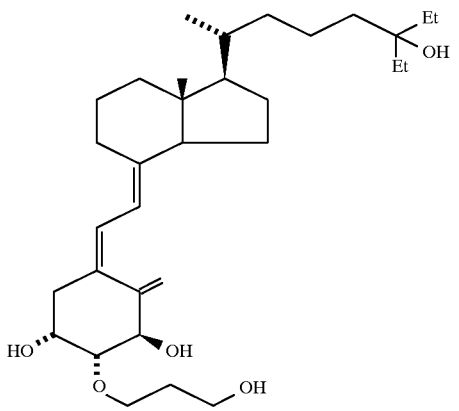

in a dose of 0.008 or 0.04 μg/kg or the compound prepared in Example 7, compound (6):

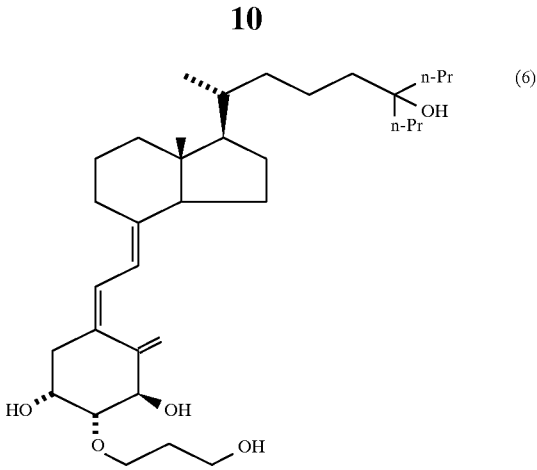

in a dose of 0.008, 0.04 or 0.2 μg/kg, 5 times a week for 6 weeks. The rats were fed an ordinary diet containing 1.2% of calcium during these experiments. After the last administration of the compound, bone mineral densities of centrum vertebrae of the rats were measured by the DXA method.

The results are shown in FIG. 1. The graphs shown in FIG. 1 illustrate the change in the bone mineral density in centrum vertebrae of OVX rats as a function of the dose of the derivative. FIG. 1 shows that both groups of the OVX rats which received compound (5) in a dose of 0.04 μg/kg and compound (6) in a dose of 0.2 μg/kg exhibited a higher increase in bone mineral density than that of the sham-OVX rats, indicating that the compounds of the present invention exhibit a bone mineral density increasing effect.

INDUSTRIAL APPLICABILITY

The compounds of the present invention exhibit a bone mineral density increasing effect and thus are useful as a pharmaceutical for osteoporosis.

We claim:

1. A compound represented by general formula (I):

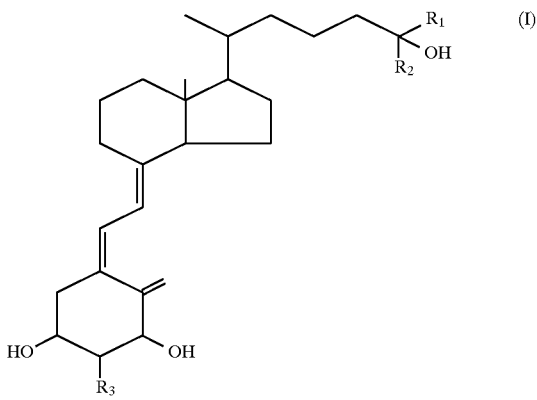

wherein R$_1$ and R$_2$, each represents an ethyl group and R$_3$ represents an alkoxy group having 1 to 7 carbon atoms which may be substituted by one or more substituents selected from a hydroxyl group, a halogen atom, a cyano group, an alkoxy group having 1 to 4 carbon atoms, an amino group and an acylamino group with the proviso that R$_1$ and R$_2$ are not a methyl group simultaneously.

2. The compound according to claim 1 wherein R$_3$ is an alkoxy group having 1 to 7 carbon atoms which may be unsubstituted or substituted by one or more hydroxyl groups.

3. The compound according to claim 2 wherein R$_3$ is an alkoxy group having 1 to 7 carbon atoms which is substituted by one or more hydroxyl groups.

4. The compound according to claim 1 which is represented by general formula (II):

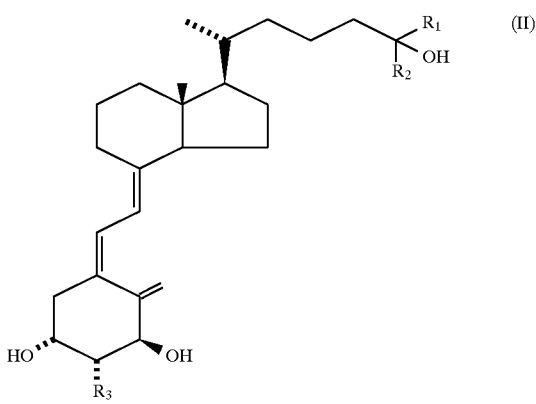

wherein $R_1$ and $R_2$, each represents an ethyl group and $R_3$ represents an alkoxy group which may be substituted by one or more substituents selected from a hydroxyl group, a halogen atom, a cyano group, an alkoxy group having 1 to 4 carbon atoms, an amino group and an acylamino group with the proviso that $R_1$ and $R_2$ are not a methyl group simultaneously.

5. The compound according to claim 4 wherein $R_3$ is an alkoxy group having 1 to 7 carbon atoms which may be unsubstituted or substituted by one or more hydroxyl groups.

6. The compound according to claim 5 wherein $R_3$ is an alkoxy group having 1 to 7 carbon atoms which is substituted by one or more hydroxyl groups.

7. The compound according to claim 6 which is represented by general formula (III):

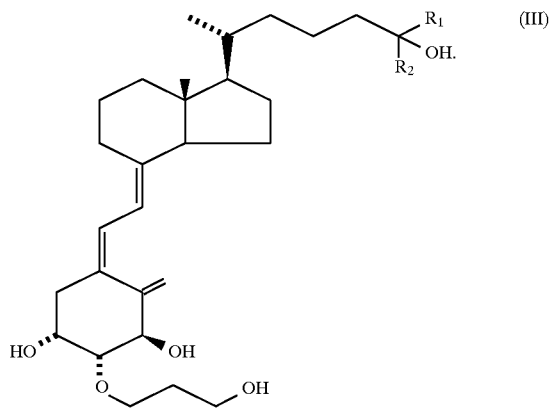

* * * * *